US010551910B2

(12) United States Patent
Slepian et al.

(10) Patent No.: US 10,551,910 B2
(45) Date of Patent: Feb. 4, 2020

(54) VIRTUAL REALITY SYSTEMS AND METHODS FOR IMPROVING CLINICAL OUTCOMES

(71) Applicant: Arizona Board of Regents on Behalf of the University of Arizona, Tucson, AZ (US)

(72) Inventors: Marvin J. Slepian, Tucson, AZ (US); Syed Hossainy, Hayward, CA (US); Fuad Rahman, Santa Clara, CA (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 15/767,347

(22) PCT Filed: Oct. 12, 2016

(86) PCT No.: PCT/US2016/056669
§ 371 (c)(1),
(2) Date: Apr. 10, 2018

(87) PCT Pub. No.: WO2017/066340
PCT Pub. Date: Apr. 20, 2017

(65) Prior Publication Data
US 2018/0292888 A1 Oct. 11, 2018

Related U.S. Application Data

(60) Provisional application No. 62/240,098, filed on Oct. 12, 2015.

(51) Int. Cl.
G06F 19/00 (2018.01)
G06F 3/01 (2006.01)
(Continued)

(52) U.S. Cl.
CPC .............. *G06F 3/011* (2013.01); *A61B 5/021* (2013.01); *A61B 5/024* (2013.01); *A61B 5/486* (2013.01);
(Continued)

(58) Field of Classification Search
CPC ..................... G06F 19/3481; A61K 2121/00
(Continued)

(56) References Cited

U.S. PATENT DOCUMENTS 6,186,145 B1 2/2001 Brown
10,130,311 B1 * 11/2018 De Sapio ........... A63B 24/0062
(Continued)

FOREIGN PATENT DOCUMENTS

WO WO 2015/153675 A1 10/2015

OTHER PUBLICATIONS

International Preliminary Report on Patentability for PCT/US2016/056669 dated Apr. 17, 2018, 10 pp.
(Continued)

*Primary Examiner* — Thomas J Lett
(74) *Attorney, Agent, or Firm* — Lathrop Gage LLP

(57) ABSTRACT

Virtual reality system and method improve clinical outcomes. The virtual reality system includes a virtual display device capable of providing virtual reality images to a patient; one or more actuators capable of providing physical experience to the patient; and a controller. The controller is capable of: automatically selecting a treatment model based upon one or both of (a) a received identity of a medical treatment applied to the patient and (b) a received identity of a targeted disease of the patient; and coordinating the virtual display device and the one or more actuators to provide a synchronized immersive virtual reality environment for the patient to experience based upon the treatment model.

20 Claims, 9 Drawing Sheets

(51) Int. Cl.
  *A61B 5/021*  (2006.01)
  *A61B 5/024*  (2006.01)
  *A61B 5/00*  (2006.01)
  *A61M 21/00*  (2006.01)

(52) U.S. Cl.
  CPC .......... *A61B 5/4836* (2013.01); *A61B 5/4848* (2013.01); *A61M 21/00* (2013.01); *A61M 2021/005* (2013.01); *A61M 2021/0016* (2013.01); *A61M 2021/0022* (2013.01); *A61M 2021/0027* (2013.01); *A61M 2205/3553* (2013.01); *A61M 2205/3584* (2013.01); *A61M 2205/3592* (2013.01); *A61M 2209/088* (2013.01); *A61M 2230/06* (2013.01); *A61M 2230/201* (2013.01); *A61M 2230/205* (2013.01); *A61M 2230/42* (2013.01); *A61M 2230/50* (2013.01)

(58) Field of Classification Search
  USPC ........................................................ 345/633
  See application file for complete search history.

(56) References Cited

U.S. PATENT DOCUMENTS

| | | | |
|---|---|---|---|
| 2009/0271213 A1* | 10/2009 | Hyde .................. | G06F 19/3456 705/2 |
| 2009/0271217 A1 | 10/2009 | Hyde et al. | |
| 2009/0292676 A1* | 11/2009 | Leuthardt ........... | G06F 19/3456 |
| 2014/0275739 A1* | 9/2014 | Hyde .................. | G06F 19/3456 600/27 |
| 2014/0315169 A1 | 10/2014 | Bohbot | |
| 2015/0306340 A1* | 10/2015 | Giap .................... | A61B 1/0005 600/301 |

OTHER PUBLICATIONS

Patel et al. (1986) "Effect of afferent renal nerve stimulation on blood pressure, heart rate and noradrenergic activity in conscious rats", Journal of the Autonomic Nervous Systems, Elsevier, Amsterdam, NL, vol. 17, No. 2, pp. 121-130.
European Patent Application No. 16856123.1, Extended Search and Opinion dated May 14, 2019, 9 pages.
International Search Report of PCT/US16/56669 dated Jan. 19, 2017, 1 pp.

* cited by examiner

CORONARY ARTERY DISEASE/ANGINA
MACRO LEVEL
702
704
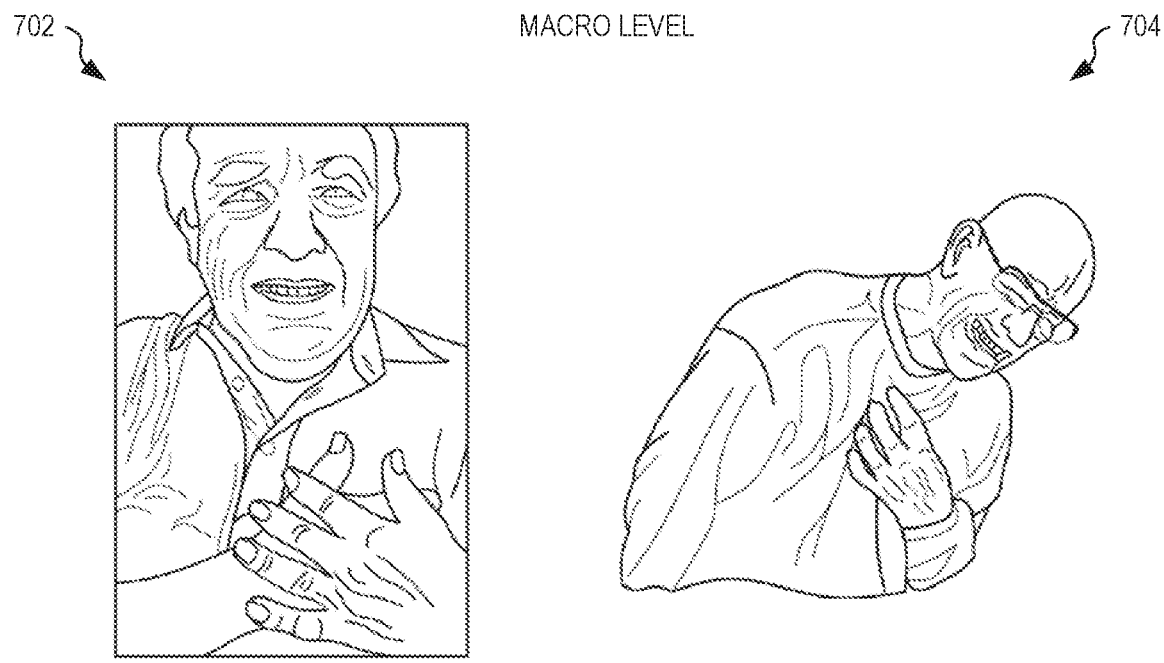
FIG. 7A
706 Cath/Angiogram
708 IVUS (Intravascular Ultrasound)
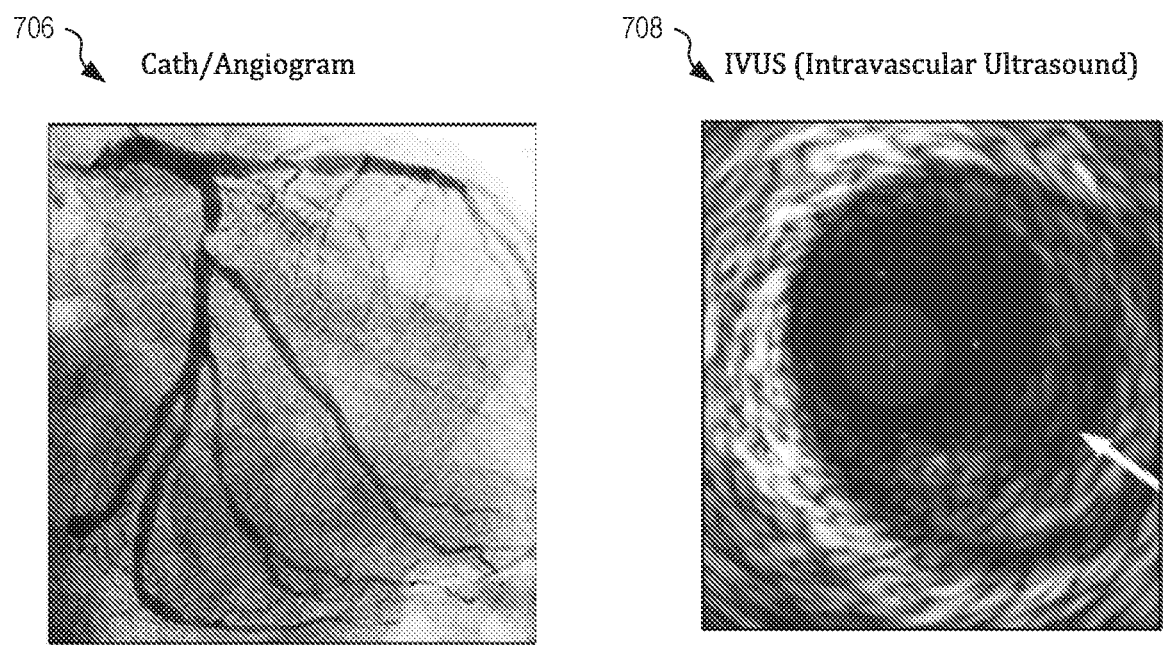
FIG. 7B
FIG. 7C

710

Histology of CAD

712

Histology – Inside the Plaque

VIRTUAL REALITY SYSTEMS AND METHODS FOR IMPROVING CLINICAL OUTCOMES

RELATED APPLICATIONS

This application claims priority to U.S. Patent Application Ser. No. 62/240,098, titled "Virtual Reality Systems and Methods for Improving Clinical Outcomes", filed Oct. 12, 2015, and incorporated herein in its entirety by reference.

BACKGROUND

When a patient is not engaged in a medical treatment, the effectiveness of that treatment is less than the effect of the same medical treatment on a patient that is engaged. Here, the term "engaged" refers to the patient being mentally involved and understanding of the medical treatment.

The placebo effect is where an improvement in medical condition is caused by a patient's belief in a medical treatment as opposed to the actual medical treatment: a patient's positive expectations of perceived treatment are translated by the patient into a positive effect.

There are many placebo effects, with different mechanisms and in different systems, medical conditions, and therapeutic interventions. For example, brain mechanisms of expectation, anxiety, and reward are all involved, as well as a variety of learning phenomena, such as Pavlovian conditioning, and cognitive, and social learning. There is also experimental evidence of different genetic variants in placebo responsiveness. The most productive models to better understand the neurobiology of the placebo effect are pain and Parkinson's disease. In these medical conditions, the involved neural networks have been identified: that is, the opioidergic-cholecystokinergic-dopaminergic modulatory network in pain and part of the basal ganglia circuitry in Parkinson's disease.

Important clinical implications emerge from these recent advances in placebo research. First, as the placebo effect is basically a psychosocial context effect, these data indicate that different social stimuli, such as words and rituals of the therapeutic act, may change the chemistry and circuitry of the patient's brain. Second, the mechanisms that are activated by placebos are the same as those activated by drugs, which suggests cognitive/affective interference with drug action. Third, if prefrontal functioning is impaired, placebo responses are reduced or totally lacking, as occurs in Alzheimer's type dementia.

SUMMARY

Beyond the placebo effect, the impact of therapy, or for that matter any suggestive intervention, counseling or positive interaction between caregiver and patient is enhanced if increased mental and physical engagement occurs from the interaction. If the patient or subject truly recognizes the condition disease or issue at hand any means that may enhance the recognition and thinking by the individual of that process will ultimately lead to a better outcome. It was originally thought that mind and body were separate and distinct. This concept was espoused by Descartes. Over time others clearly recognized that there is a continuum of mind and body. This was the view of Herbart, Liebniz and Spinoza. This viewpoint has been reinforced and expanded by modern science—specifically psychology, neuroscience and medicine. As such with enhanced neural processing and higher brain function complex situations and concepts can take on a "somatic" body element.

Through thought, mulling over, cycling in the mind's eye, the individual may envision the situation, having greater impact and imprinting on them. Beyond this, even greater somatic recognition and sensation, i.e., feeling it, experiencing it in the body so that the individual "really gets it," will lead to a better outcome. For the purposes of further discussion here this may be termed "therapeutic somatization." This is distinct from pathologic somatization, which is a psychiatric disorder that goes beyond where experiences and thoughts are converted to true physical maladies signs and symptoms. For example, when someone sees a positive potential outcome with improvement in a condition, if they really "get it" they may go on to feel energized or strong, converting a mental thought into a physical feeling.

Beyond higher consciousness, thought and cognition, if one can expose a patient to a correlative event or process that leads to a neural imprinting event. Where this physical stimulus is processed below the highest level of consciousness, it is resilient to the effects of dementia. For example, the physical stimulus may lead to a sense of pleasure, or other type of non-negative recognition, where pleasure type centers in the brain are stimulated, resulting in increased activity in the caudate nucleus and/or release of favorable hormones, such as oxytocin. This additional stimulatory effect may aid and synergize with a conventional medical/surgical therapy and lead to an additional form of "therapeutic somatization" to provide an added positive effect coordinate with conventional therapy.

People generally do not consciously walk around thinking of their own individual healthcare. One task of a doctor treating a patient is to raise the patient's awareness of his or her healthcare, particularly if being treated for disease or condition. The successful doctor aims to engage the patient behaviorally, emotionally, and psychologically in the medical treatment being administered. Without such engagement, the effectiveness of the medical treatment is simply less than optimal.

In one embodiment, a virtual reality system improves clinical outcomes. The virtual reality system includes a virtual display device capable of providing virtual reality images to a patient; one or more actuators capable of providing physical experience to the patient; and a controller. The controller is capable of: automatically selecting a treatment model based upon one or both of (a) a received identity of a medical treatment applied to the patient and (b) a received identity of a targeted disease of the patient; and coordinating the virtual display device and the one or more actuators to provide a synchronized immersive virtual reality environment for the patient to experience based upon the treatment model.

In another embodiment, a virtual reality method improves clinical outcome for a patient. One or both of (a) an identity of a medical treatment applied to the patient and (b) an identity of a targeted disease of the patient are received. A treatment model is automatically selected based upon the identified medical treatments and targeted diseases. An immersive virtual reality environment based upon the treatment model is generated using both a treatment therapy virtual display device to provide virtual reality images to the patient and one or more actuators that provide physical experience to the patient. The patient is immersed in the immersive virtual reality environment.

BRIEF DESCRIPTION OF THE FIGURES

FIGS. 7A-G shows exemplary images output by the system of FIG. 1 illustrating exemplary multi-scale levels, in an embodiment.

DETAILED DESCRIPTION OF THE EMBODIMENTS

A doctor may apply medical treatment to a patient for diseases and conditions such as a disease selected from the groups including: Cardiovascular disease (Coronary Artery Disease/Angina, Heart Failure, Valvular Disease, and Arrhythmias including Atrial Fibrillation, supraventricular tachycardia and ventricular tachycardia), Pericardial disease; Pulmonary disease including Asthma, chronic obstructive pulmonary disease, Interstitial Lung Disease, Hypersensitivity pneumonitis, Pneumonia, Pleuritis, and Lung cancer, Gastrointestinal diseases including Peptic Ulcer Disease, Gastro esophageal Reflux Disease, Irritable Bowel Disease, Crohn's Disease, Ulcerative Colitis, Malabsorption Syndromes, Bacterial Overgrowth, celiac disease, gastrointestinal cancers, Hepatitis, Pancreatitis (including Acute and Chronic forms), and Gallbladder disease; Hematological and oncological diseases including Anemia, Leukemia and lymphoma, Thrombocytopenia, myelodysplastic syndrome, Polycythemia, Cancers including but not limited to breast, Lung, Prostate, Pancreas, Liver, Kidney, Brain, Bone, Adrenal, Skin, and Melanoma; Neurological diseases including Chronic Pain Syndromes, Neuralgias, Mononeuritis multiplex, Neurocognitive decline, Dementias, Cerebrovascular Accident (CVA), Post CVA syndromes, Parkinson's Disease, Amyotrophic Lateral Sclerosis, multiple sclerosis, and Myasthenia; Rheumatologicial diseases including Chronic arthritis, Fibromyalgia, degenerative joint disease, Rheumatoid, Systemic Lupus Erythromatosis, Sjogren's disease, Reiters, scleroderma, mixed connective tissue disease, and Wegners Granulomatosis; Endocrine diseases including—Hypothyroidism, Hypothyroidism, Diabetes Mellitus, Cushing's disease, Adrenal Insufficiency, Prolactinoma, Hypogonadism, and Sex steroid disorders; Genitourinary disorders including renal stones, renal failure, polycystic kidney disease, renal carcinoma, ureteral diseases and obstruction, bladder cancer, urethral strictures, testicular cancer, prostatism/BPH, prostate cancer, and erectile dysfunction; Dermatological disorders including, eczema, psoriasis, erythemasnodosum, multiforme, ptyriasis, malignancies, pemphigus, pemphigoid, dermatophytosis, fungal infections, and bullous diseases; Gynecological disorders including, ovarian carcinoma, tubo-ovarian disorders, uterine carcinoma, endometriosis, uterine fibroids, and menstrual cramps; and Psychological disorders including Anorexia Nervosa, Neuroses, Depression, Mania, Cyclothymic behavior, Panic Disorder, Eating Disorders, Psychoses, and other psychiatric disorders, such as depression. The above list is representative and by no means fully inclusive. To improve clinical outcome of the medical treatment, virtual reality systems and methods for improving clinical outcomes are applied to the patient to invoke additional improvement, as now described.

Figure 1:
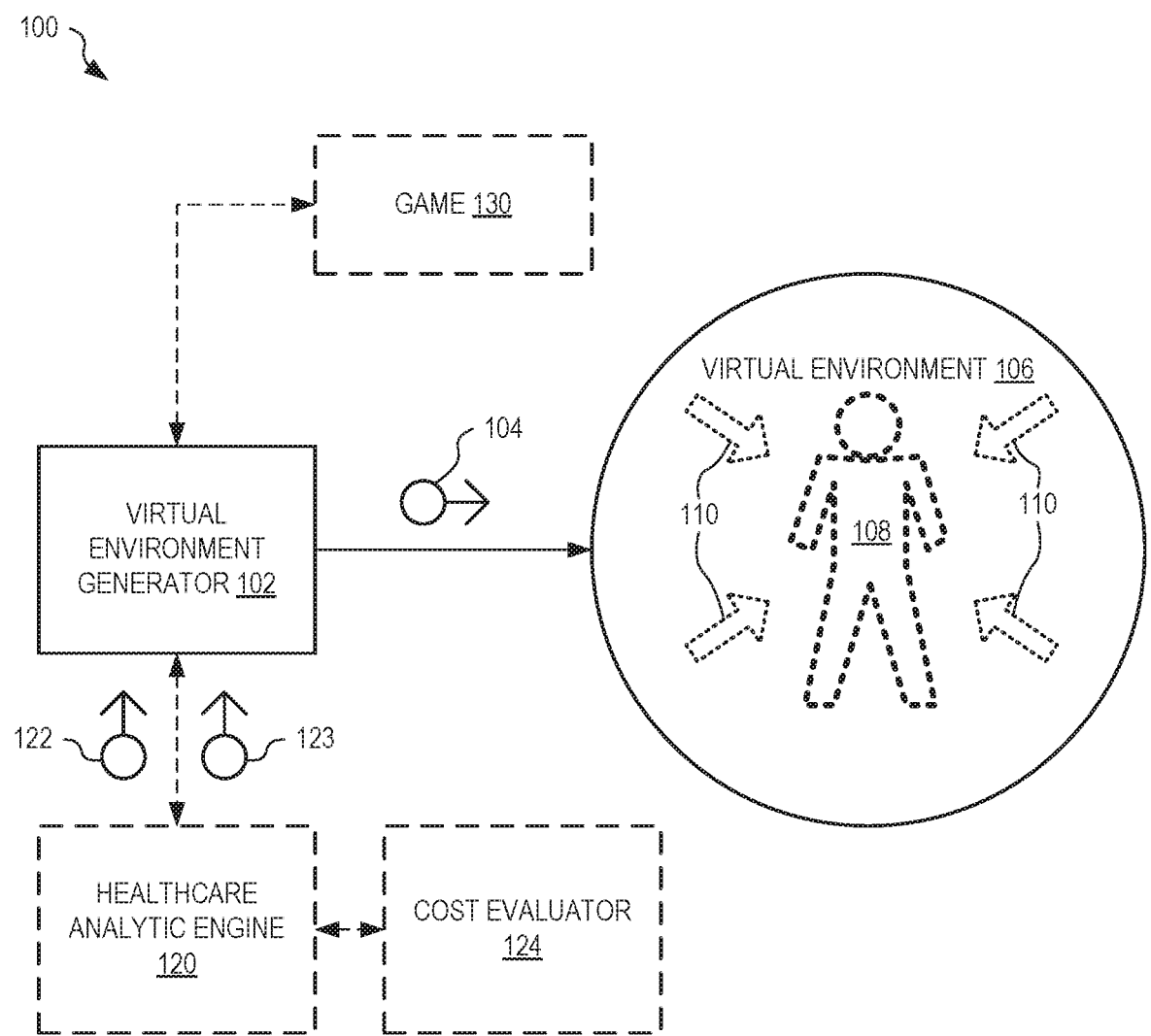
FIG. 1 shows one exemplary virtual reality system for improving clinical outcomes, in an embodiment.

FIG. 1 shows one exemplary virtual reality system 100 for improving clinical outcomes. System 100 includes a virtual environment generator 102 and an immersive virtual environment 106. Virtual environment 106 may be composed of a physically contained entity or be an entity defined by the proximate items and constituents bought into play to create the virtual effect. Virtual environment 106 may include one or more of a virtual reality dome, virtual reality goggles, multiple media displays, helmets, wearable displays or projection means, sensory duplicators or emulators—for all senses including sight, sound, smell, taste, temperature and the like, haptic (tactile) devices, feedback sensors, and so on.

Virtual environment generator 102 generates control signals 104 for controlling virtual environment 106 such that a patient 108 within virtual environment 106 is immersed within a virtual experience 110 that enhances medical treatment(s) applied to patient 108. Virtual environment generator 102 may communicate with a healthcare analytic engine 120 to receive a complete health status 122 of patient 108 and/or a treatment definition 123, which is automatically selected by system 100 based upon complete health status 122, applied treatments, and results of other patients having similar conditions to patient 108.

Figure 2:
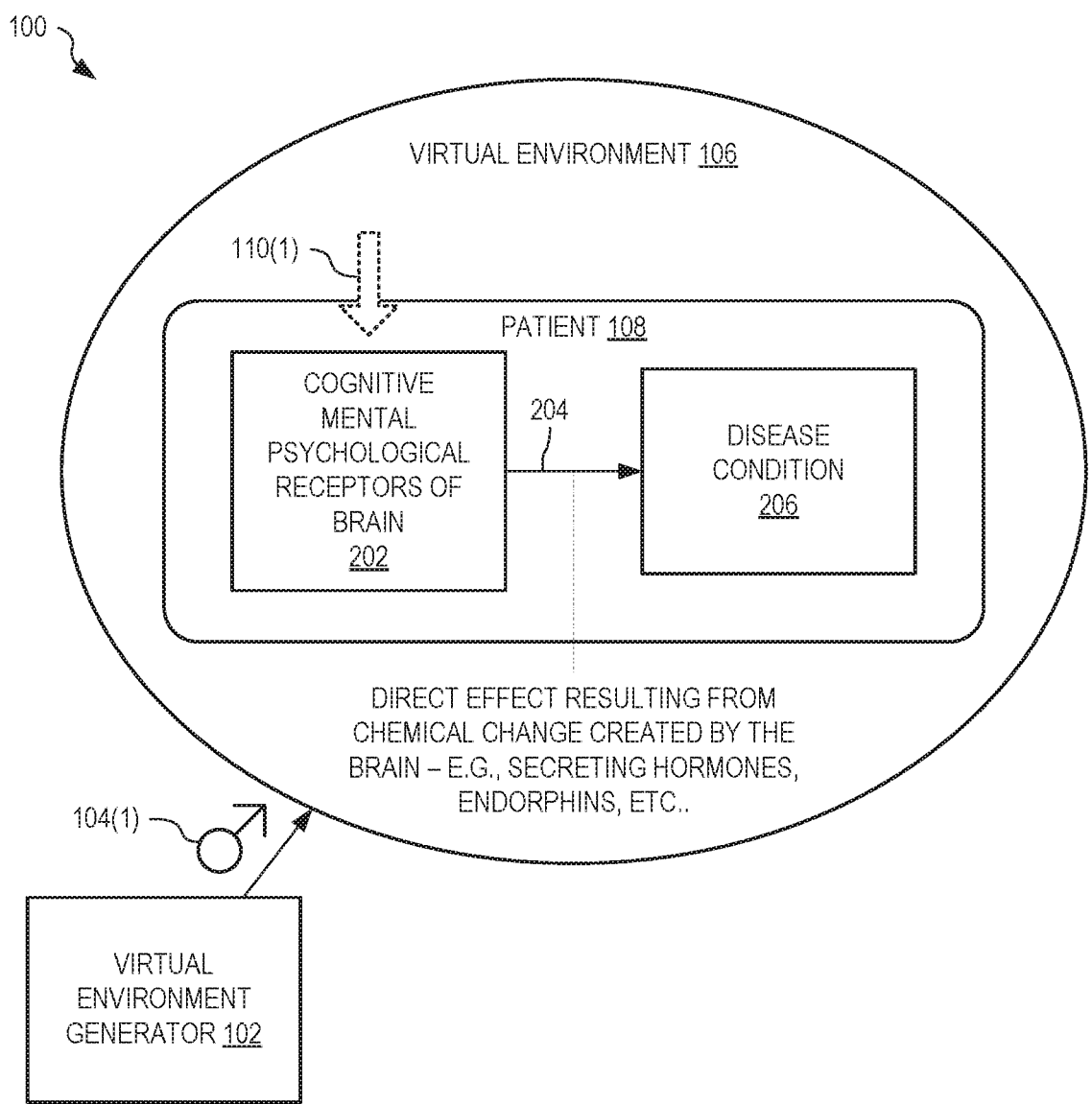
FIG. 2 shows exemplary operation of the virtual reality system of FIG. 1 for improving clinical outcome of medical treatment applied to a patient to correct a specific disease, in an embodiment.

FIG. 2 shows exemplary operation of system 100 for improving clinical outcome of medical treatment applied to patient 108 to correct a specific disease, such as coronary artery disease, where control signals 104(1) control virtual environment 106 to provide experience 110(1) to cognitive, mental, and psychological receptors of the brain 202 of patient 108. Experience 110(1) is specifically selected to cause brain 202 to generate a chemical response 204 (represented as an arrow in FIG. 2), such as one or more of hormones, endorphins, etc., that directly affects a condition 206 of the disease. In one example, chemical response 204 causes patient 108 to better process, recognize, understand and "truly get" the fact that he or she has this disease, and/or the extent to which he or she has the disease, and/or truly comprehend the impact of the disease, both without therapy and with therapy. Patient 108 is thereby better set up, better equipped, and better primed to accept, undertake and carry out therapy for the disease more effectively. In a second example, chemical response 204 improves the outcome of medical treatment applied to patient 108 to treat the coronary artery disease (as condition 206), since the chemical response acts as an adjunct therapy to synergize with the prescribed therapy. Here, the positive chemistry (i.e., chemical response 204) elicited has an additional positive effect somatically for patient 108.

Figure 3:
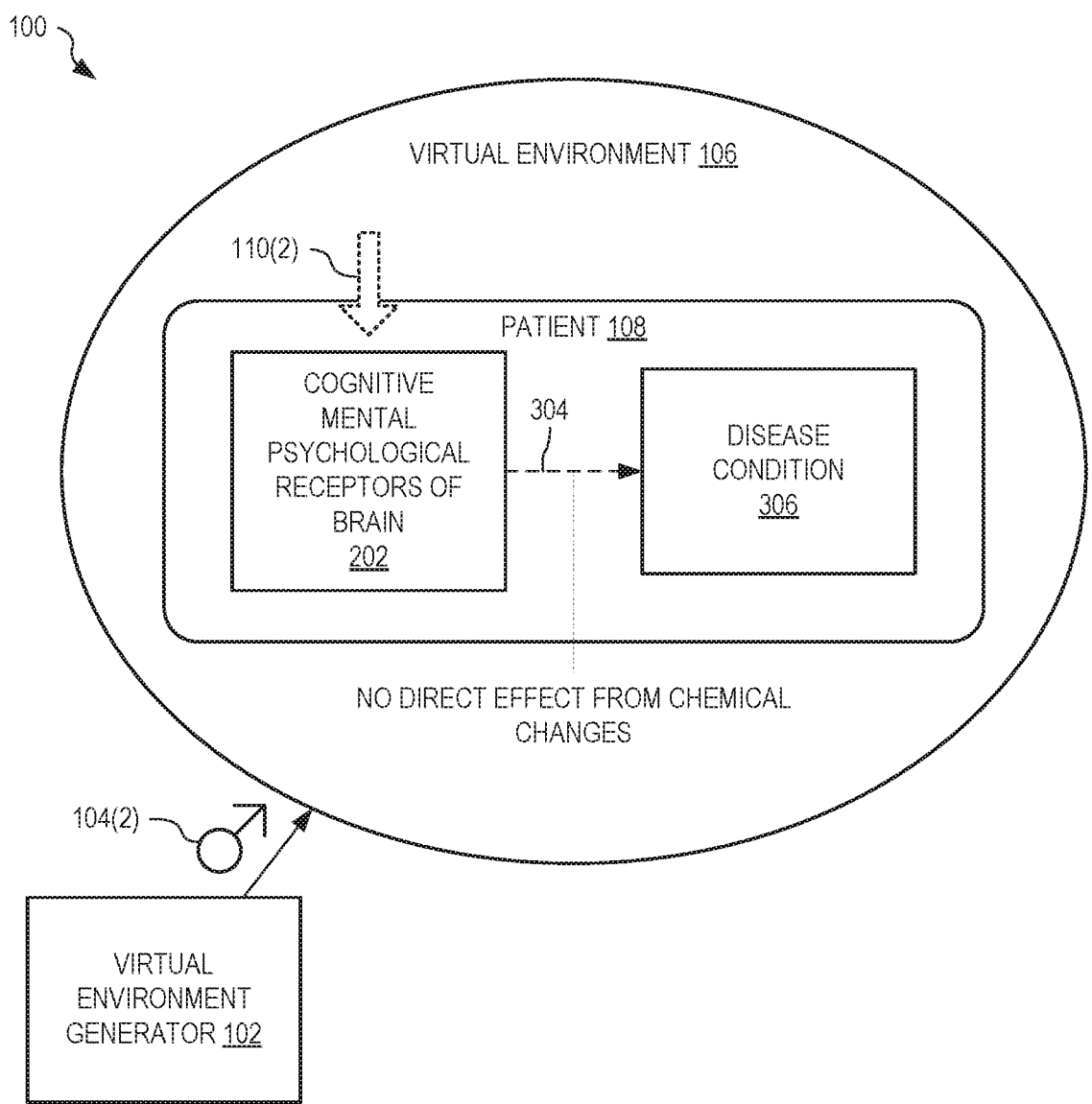
FIG. 3 shows exemplary operation of the virtual reality system of FIG. 1 for treating a patient having a particular disease, such as anorexia, in an embodiment.

FIG. 3 shows exemplary operation of system 100 for treating patient 108 having a particular disease where medication may not be prescribed, such as Anorexia Nervosa. Thus, patient 108 has not received conventional medical treatment, such as medication. Control signals 104(2), generated by virtual environment generator 102, control virtual environment 106 to provide experience 110(2) to cognitive, mental, and psychological receptors of the brain 202 of patient 108, where experience 110(2) is specifically selected to cause the patient's brain 202 to have an effect 304 (indicated by a dashed arrow in FIG. 3) on a condition 306 of the disease. Although disease condition 306 is not directly affected by chemicals secreted by brain 202, experience 110(2) does improve disease condition 306 indirectly. This improvement may come from a variety of means—some understood and some beyond current mechanistic understanding. One mechanism at work may be "sensory substitution." In this case, patient 108, by virtue of repetitive exposure to experience 110(2), processes and somaticizes the information from the contact and intervention. However, in this case patient 108 substitutes a sensation or feeling derived from this processing with an alternative feeling—one that is pleasurable. For example, a disease game (e.g., game 130, described below) may improve adherence to therapy or a change in lifestyle by allowing the player (i.e., patient 108) to experience this and may associate this with one or more of a positive sound, a pleasant vision, and a pleasurable smell, thereby substituting one type of somaticized response for an alternative sensory feeling.

Figure 4:
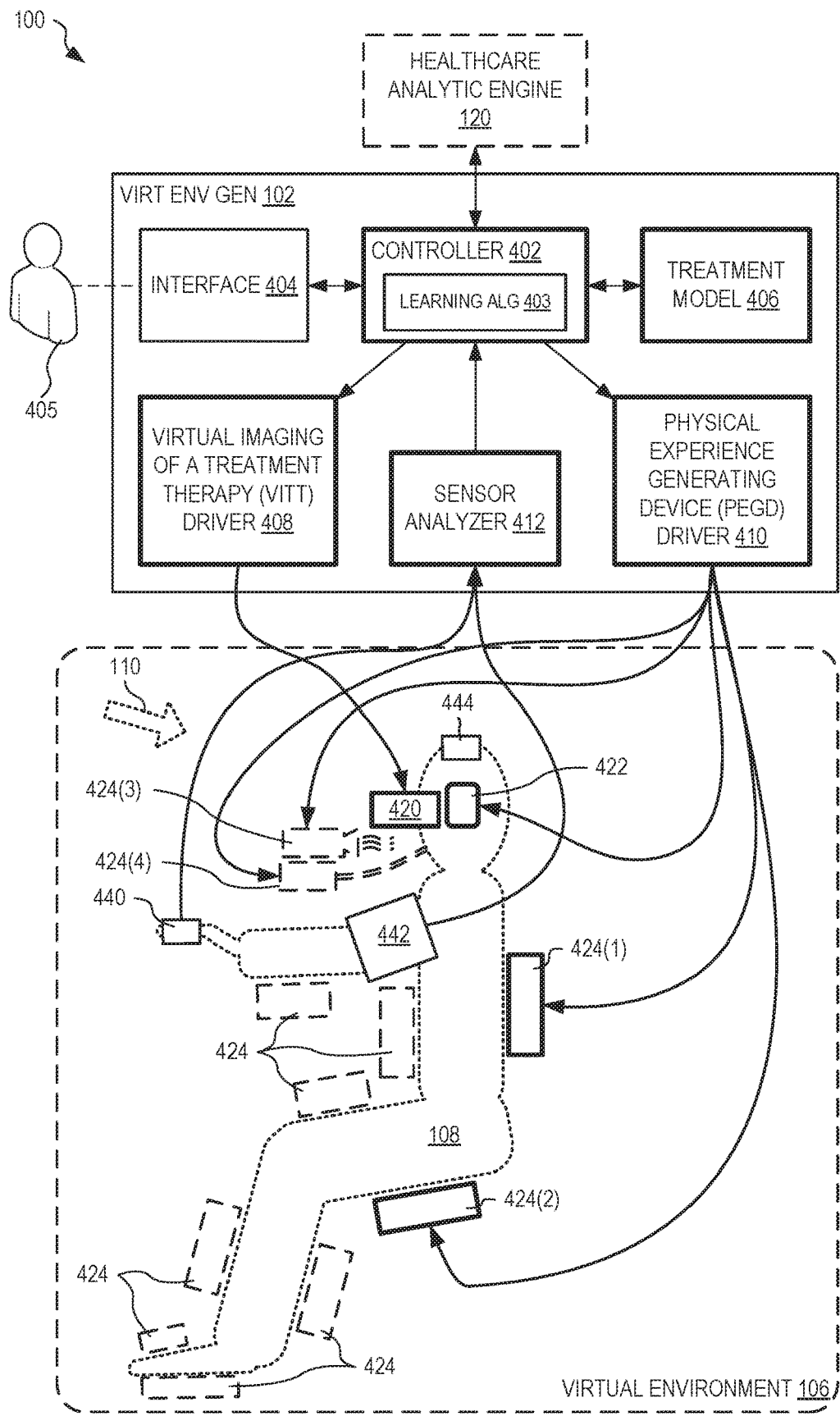
FIG. 4 shows the virtual reality system of FIG. 1 in further exemplary detail.

FIG. 4 shows virtual reality system 100 in further exemplary detail. Virtual environment generator 102 of system 100, FIG. 1, includes a controller 402, an interface 404, a treatment model 406, a virtual imaging of a treatment therapy (VITT) driver 408, a physical experience generating device (PEGD) driver 410, a sensor analyzer 412, a virtual imager 420 (e.g., a virtual reality headset), audio output devices 422 (e.g., audio headphones), and one or more actuators 424 (e.g., electrical, optical, magnetic, chemical, mechanical, radiation, shock, pressure, vibration, heating or cooling, an olfactory stimulator—for generating a smell such as perfume and floral scents, a taste stimulator—for generating tastes such as a pleasurable sweet taste or a sour bitter taste, a massage element, a pain modulating/relieving/distracting element, acupuncture, sono, ultrasound, transcutaneous electrical nerve stimulation (TENS) and so on). VITT driver 408 drives virtual imager 420 to provide virtual imagery to patient 108 and PEGD driver 410 drives actuators 424 to provide physical stimulus to patient 108. For example, PEGD driver 410 controls one or more actuators 424 to provide one or more of electromechanical, electrochemical, or electromagnetic stimulation to patient 108. System 100 thereby additively and/or synergistically enhances the effect of the virtual imagery and the physical stimulus to enhance the overall effect of the treatment on patient 108.

It should be understood that VITT may present both diagnostic, factual and therapeutic information, images, and other sensory renderings, and any combination thereof "Therapy," in a generic sense, often requires presentation of information to the patient for enhanced processing and recognition, and this is provided by system 100.

System 100 may be used to administer drugs and foods, such as to induce a hypoglycemic state to teach diabetes mellitus (DM) patients to recognize when they are going into a hypoglycemic state. Conversely, system 100 may be used to treat an obese patient by creating a feeling of mild distaste or disgust for food (e.g., by generating unfavorable smells, bordering on noxious/putrid odors). In an embodiment, actuator 424(3) delivers gaseous materials to patient 108. For example, actuator 424(3) may deliver a smell effect to patient 108. In an embodiment, actuator 424(4) delivers solids and/or liquids to patient 108. For example, actuator 424(4) may deliver one or more of medication, a sugar pill (placebo), menthol water, and so on to patient 108. Further, the emitted smell or sound may be varied with repetitive treatment, so as not to induce a habit, accustomization, attenuation, decreased responsiveness or "tachyphylactic response" to the stimulus.

System 100 may also include an oxygen saturation sensor 440, a blood-pressure sensor 442, one or more accelerometers 444, and other feedback sensors (not shown, such as one or more of voice sensor, heart rate sensor, temperature sensor, sweat secretion sensor, glucose level in blood and tear solution sensor, hydration sensor, blood-borne biomarkers of pain sensor, and so on). Sensors 440, 442, 444 are communicatively coupled (e.g., wired or wireless) with sensor analyzer 412 which provides feedback data to controller 402 based upon information from one or more of sensors 440, 442, 444.

Controller 402 operates to synchronize VITT driver 408 and PEGD driver 410 to provide experience 110 that is a fully immersive virtual reality experience for patient 108. For example, the audio, tactile, olfactory, and taste experience provided by PEGD driver 410, output devices 422, and actuators 424 are synchronized with the visual images provided by VITT driver 408 and virtual imager 420. Sensors 440, 442, 444 and sensor analyzer 412 provide feedback to controller 402, which in turn controls VITT driver 408 and PEGD driver 410 using a feedback control loop. Although shown as separate devices, sensors 440, 442, and 444 may be combined with one or more of virtual imager 420, output devices 422, and actuators 424 without departing from the scope hereof.

In an alternative embodiment, VITT driver 408 and PEGD driver 410 communicate with one another (e.g., wired and/or wirelessly and/or via controller 402) to provide an immersive virtual environment 106 for patient 108.

In an alternative embodiment, system 100 includes additional drivers and actuators (e.g., similar to drivers 408, 410, and actuators 424) to create taste, smell, sound, or any other sensory input, either alone or in combination for patient 108. System 100 similarly coordinates these drivers and actuators (wired or wirelessly) to provide immersive virtual environment 106 for patient 108.

Interface 404 allows control of system 100 by an operator 405 (e.g., a doctor or therapist) using one or more devices selected from the group including: a laptop computer, a handheld computer, a smart phone, and a tablet computer. Operation may occur in any setting, including but not limited to: the hospital, a clinic facility, office facility, rehab facility or the patient's home or office. Operator 405 may be proximate or remote from system 100. Operator 405 may approve selected treatments prior to initiating the therapy session on patient 108. Operator 405 monitors patient 108 during the therapy session and receives a real-time status from system 100 (e.g., via interface 404) as to progress of the therapy session and provides real-time input and manipulation of system 100 to further potentiate the therapy effect.

In an embodiment, system 100 generates (a) an estimated cost for treating patient 108 and (b) an estimated cost saving based upon the treatment. For example, controller 402 interacts with healthcare analytic engine 120 to determine the estimated cost of treating patient 108 and to determine the estimated cost saving based upon the treatment. Healthcare analytic engine 120 may cooperate with a cost evaluator 124 to track healthcare costs and to estimate cost of particular treatments. Controller 402 then presents this cost information to operator 405 via interface 404, for example. Determined cost savings are based upon healthcare analytics of patients having treatments by system 100 and patients not having treatments by system 100, and may draw upon actual results determined from healthcare analytic engine 120.

To determine the overall cost of therapy generated by system 100 for patient 108, the system (controller 402) first determines the mode of coverage of the patient—i.e. Self-pay, Medicare or Medicaid, Commercial insurance or any other form of health plan/health insurance coverage/benefits. This information and categorization allows fees and costs of a specific therapy to be determined from an information source such as one or more of a database and a look-up table. System 100 then uses intelligence from the medical records of patient 108 and intelligence derived from Big Data (such as via the web, via a subscription and/or generated from corporate, group, local or individual use data) to determine the likely length/extent of therapy and possible/probable outcomes. Based on cost estimates for the therapy and the outcome, potential cost savings from use of system 100 may be calculated, either in adjunct mode or stand-alone mode as compared to the cost of not using system 100. This comparative economic intelligence is continually updated such that with continued use of system 100 and a growing number of treated patients, system 100 becomes smarter. By providing estimated cost for treatment and cost savings when applying the treatment against the cost of not using the treatment, system 100 provides operator 405 with valuable evidence for using the treatment on patient 108. Specifically, the use of system 100 reduces overall healthcare cost for patient 108 by improving outcome of medical treatment, thereby reducing the overall cost of healthcare to patient 108.

In addition to reducing actual cost of a specific, individual therapy, at a given time, system 100 significantly reduces the overall cost of care for patients (e.g., patient 108) by significantly reducing readmission rates of patients to the hospital. For example, heart failure is a leading cause of admission of patients to the hospital in the United States. It is a chronic condition with progressive decline. Primarily, for patients with a more advanced condition, a medical therapy is used (i.e., the patient takes a multi-pill regime on a daily basis). Unfortunately, for a large percentage of these patients there is non-adherence, lack of attention to detail, and/or frank disregard of the prescribed regime. Therefore, twenty to thirty percent of these patients are readmitted to the hospital within 30 days of discharge. This readmission rate for heart failure, as well as for many other highly targeted chronic diseases, has been the focus of the Centers for Medicare and medicate Services (CMS) and other health cost payers in the United States and worldwide. As a result, health cost payers are extracting consequences, docking hospitals and physicians, limiting their reimbursement, and progressively decreasing reimbursement for these diseases. By using system 100, patients, on a multidimensional, multi-experiential level, see, feel and otherwise "get" their disease. Patients may experience the consequences, on multiple levels (described below) of either or both (a) adherence to treatment and (b) non-adherence to treatment. Patient 108 may also experience the impact of adherence, and non-adherence, to treatment on friends, family and social situations. Patient 108 is immersed in their disease and experiences multiple elements of their condition on a somatic level, and therefore the odds and reality of readmission for patient 108 is reduced. System 100 thereby provides a significant saving in cost, increases medication compliance, and reduces unnecessary strain and demand on the health care system.

One or more of actuators 424 and sensors 440, 442, and 444 may be placed near (within visible or audible range), on, affixed to, placed within (existing or formed orifices) or implanted within patient 108. In a preferred embodiment, such implants consist of flexible and/or stretchable electronics printed on durable or bioresorbable polymers that operate to generate a tactile experience for patient 108, as described above, and may operate to measure data from patient 108. In this situation, PEGD driver 410 may operate to activate (e.g., using a wired or wireless coupling) the implanted actuators and sensor analyzer 412 operates to receive data from implanted sensors. Such implants may also be used for a purely diagnostic episode or a combination diagnostic therapeutic mode.

Actuators and sensors may also be on, in, and otherwise connected or associated with—i.e. via near field, Bluetooth or similar communication means, other configurations that may be associated with the subject to provide virtual experience 110. These may include but are not be limited to a headband, skull cap, hat, mask, glasses, goggles, earpiece, earmuff, ear canal insert, oral appliance, scarf, neck collar, neck stocking, shirt—full or partial, body band, belt, pant—any means of, body stocking, shawl, wrap, kimono, sari, Panjabi, pajama, lungi, salwar kameeze, fatua, sock, glove, finger cot, toe cot. Also to be included are proximate drapes, curtains, shields, body armor, coats, cloaks, body bubble, body egg, or other full or partial encasement.

Treatment model 406 is configured with extensive visual imaging to affect optimal improvement in clinical outcomes for patient 108 for the selected medical treatment and/or targeted disease. Controller 402 provides sensed feedback data, received from sensor analyzer 412, to healthcare analytic engine 120. Healthcare analytic engine 120 is for example a medical database that stores relevant medical information relating to use of system 100 and further includes data relating to results of using system 100, such as input by doctors and other medical supervisors of patient 108 and other patients. Healthcare analytic engine 120 stores information relating to the selected treatment model 406 and results of using that treatment model on other patients having similar medical treatments and/or targeted diseases.

In one example of operation, healthcare analytic engine 120 selects treatment model 406 for patient 108 based upon prescribed medical treatments and diagnosed disease or diseases of patient 108. In this example, healthcare analytic engine 120 may propose treatment model 406 based upon prior experience of similar treatment models on other patients having similar medical treatments and similar disease diagnosis. System 100 cooperates with healthcare analytic engine 120 to continually learn and improve treatment models based upon experience.

Controller 402 is based upon decision making. In one example of operation, system 100, and/or a clinician, first identifies the specific disease to be treated for patient 108. The overall diagnostic and treatment plan is reviewed by the treatment team, physician or healthcare worker. Although system 100 is primarily aimed at therapeutics, it also may be utilized for diagnostics, i.e. to evoke further symptoms and signs that may help clarify a diagnosis. (See below for additional details.) Once the overall treatment plan is constructed and vetted, system 100, and/or the clinician, next identifies one or more elements of the treatment plan that may be best treated using system 100. Once the specific virtual reality target is identified a treatment plan and scheme is selected in terms of the types of mind-body connections desired, the sensory shift or substitution that is hoped to be evoked, the response and the range of response is outlined. System 100 then immerses patient 108 in the virtual-reality therapy (experience 110) and monitors patient 108 with identified endpoints outlined a priori to enable efficacy of the treatment to be continuously and/or periodically monitored. For example, system 100 may immerse patient 108 in the virtual-reality therapy (experience 110) to induce mild fear and/or anxiety as deemed therapeutically necessary to get a reaction from patient 108. Thus, system 100 may provide negative stimulus as well as positive stimulus to patient 108.

A variety of means may be employed to monitor the efficacy of treatment by system 100 including but not limited to medication compliance, monitoring of key identified endpoints for a given condition (e.g., blood pressure control for hypertension, weight for obesity, weight for anorexia, etc.). In addition, monitoring devices (e.g., wearable and/or proximate such as in the home of patient 108), placed monitors, and/or video (e.g., via Skype™) or the like, may be utilized to monitor the efficacy of treatment by system 100.

System 100 may also utilize biofeedback methodologies and devices to monitor treatment efficacy. System 100 may use devices and endpoints that operate and monitor one or more of, but not limited to, brainwaves, heart function, breathing, muscle activity, and skin temperature.

Figure 6:
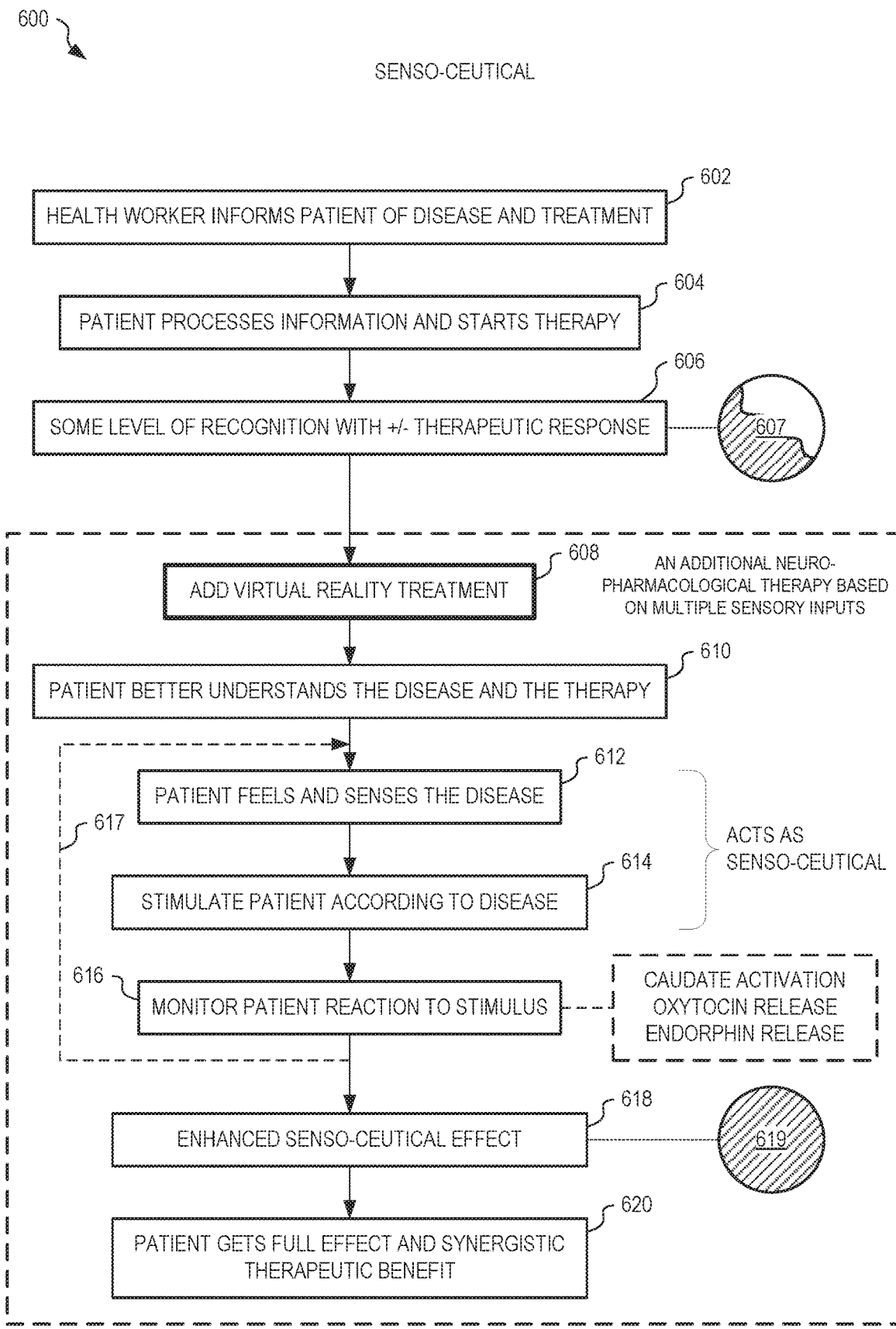
FIG. 6 is a flowchart illustrating exemplary operation of the system of FIG. 1, in an embodiment.

FIG. 6 is a flowchart illustrating exemplary operating method 600 for system 100 of FIG. 1 to improve clinical outcomes. Steps 602 through 606 of method 600 represent the well-known prior art approach where a health worker informs a patient of their disease and the associated treatment (step 602), the patient processes the information and starts the therapy (step 604), whereupon some level of recognition of the disease and therapy by the patient may have positive and negative responses, typically achieving a less than optimal result as indicated by partially filled circle 607.

Step 608 implements a virtual reality treatment, using system 100, that adds an additional neuro-pharmacological therapy based on multiple sensory inputs. Through use of system 100, the patient better understands the disease and the therapy (step 610) by feeling and sensing the disease (step 612) where the patient is stimulated according to the disease (step 614) and the patient's reaction to the stimulus is sensed (step 616), such as by monitoring one or more of caudate activation, oxytocin release, and endorphin release. Steps 612 through 616 may repeat, as indicated by arrow 617, based upon the patient's reaction. Steps 612 and 614 act as senso-ceutical to result in an enhanced senso-ceutical effect (step 618) upon the patient with a more complete result as indicated by filled circle 619. Thus, the patient gets full effect and synergistic therapeutic benefit (step 620).

Figure 7D:
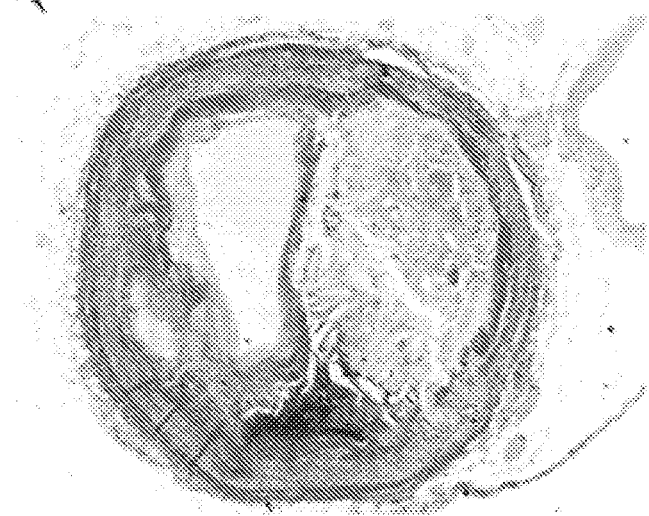
Figure 7E:
Figure 7F:
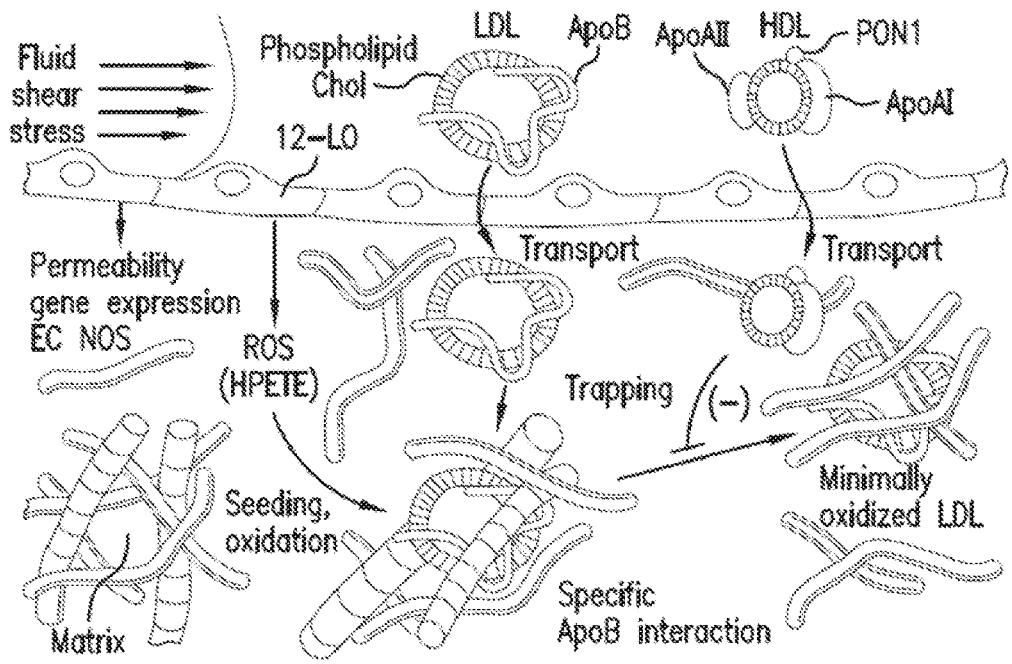
Figure 7G:
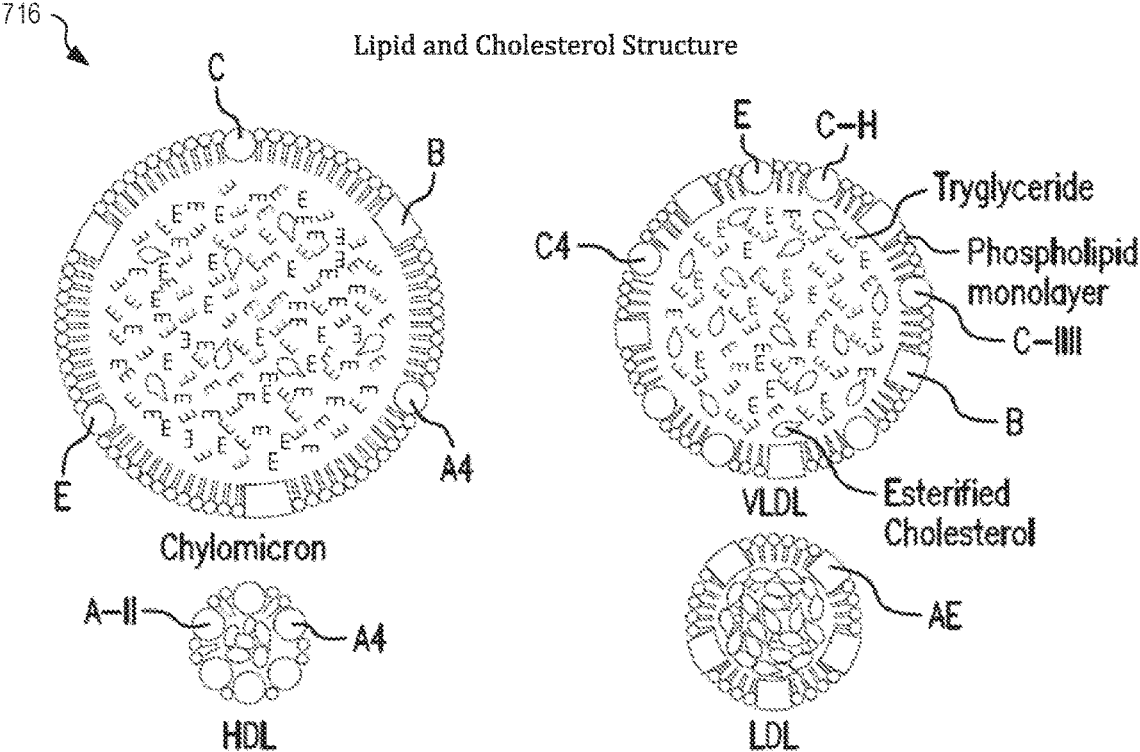

System 100 operates on a "multi-scale" level, where system 100 selects treatment model 406 to portray, and the patient to experience, elements of the physiology, pathophysiology, disease process, therapeutic process, and the consequences of wellness versus morbidity on multiple levels of involvement. For example, system 100 may portray one or more of the following levels: (1) the whole body level (e.g., see FIG. 7A, images 702 and 704), (2) a body region, e.g. abdomen, (3) an organ, (4) an organ component, e.g. hepatic artery, (5) at a cellular level, (6) at an intracellular level, (7) at a molecular level, and (8) at an atomic level.

FIGS. 7A-7G show exemplary images 702-716 output by system 100 of FIG. 1 illustrating multi-scale levels for coronary artery disease/angina. Images 702 and 704 represent a macro level where the patient sees a person experiencing symptoms of coronary artery disease/angina. Image 706 represents an angiogram where the patient experiences a next of the multi-levels. Image 708 represents an intravascular ultrasound where the patient experiences a next of the multi-levels. Image 710 represents a next of the multi-levels illustrating histology of coronary artery disease where a blood vessel is partially blocked by plaque. Image 712 represents a next of the multi-levels illustrating histology of the plaque. Image 714 represents a next of the multi-levels and illustrates lipid deposition in the artery wall with resultant inflammation. Image 716 represent a next of the multi-levels illustrating lipid and cholesterol structure at a molecular/atomic level.

System 100 may be configured to operate at a level that best portrays the impact of disease, wellness, adherence or non-adherence of treatment of the individual patient as to its effect on another individual, family, group and even society. That is, system 100 controls experience 110 to "zooming out" and imprint the effects of the patient's disease on other individuals, the patient's compliance to therapies, or not, and so on.

Where patient 108 has atherosclerotic disease of the coronary artery, patient 108 typically presents with angina or shortness of breath, often before a heart attack or heart failure. Beyond conventional counseling on use of lipid lowering agents (e.g., statins), system 100 provides a very effective impression upon patient 108 of a need for lifestyle change. For example, system 100 immerses the patient in a virtual reality experience that effectively provides a shakeup and a wake up of patient 108 as to the necessary steps to avoid eventual heart damage. The advantage of using system 100 lies in its synergistic affect with medications as well as its potential to obviate the need for medication, particularly in those patients who have serious side effects with the use of statins. This is a significant advantage, since the number of patients that have side effects from using statins is significant, with possible muscle damage and liver dysfunction occurring.

Continuing with this example, patient 108 enters into virtual reality therapy, the diagnostic and therapeutic treatment plan is established, and treatment using system 100 is started. System 100 may implement, for patient 108, a multi-scale treatment plan that involves exposing patient 108 to the state of his or her disease at present, showing patent 108 life and the effects on physiology under normal conditions, then, by reverting to pathophysiology of patent 108, showing consequences of the disease at all levels. For example, within virtual environment 106, patient 108 may first experience effects of the disease on the whole body, then the effects of the disease on the heart, then the effects of the disease on the artery in the heart, then the effects of the disease on the wall of the artery, and then showing lipids and inflammatory cells enter and deposit in the blood vessel to form an atherosclerotic plaque (e.g., see images 702 through 716 of FIGS. 7A-G).

System 100 may then simulate the element of time to show the evolution of the disease by showing patient 108 the progressive buildup of plaque, increasing heat forming like a near plus pocket atheroma in the vessel wall, the potential for plaque rupture, the consequences of thrombosis and clotting, and a heart attack and heart damage that can occur. System 100 may then show the social consequence of the disease on the patient and his family. Similarly, if desired for patient 108, system 100 may control virtual environment 106 to provide the multi-scale approach to move down in scale allowing patient 108 to experience the molecular layering of lipids, and the interaction of various molecules both extra-cellularly and intra-cellularly. By generating virtual environment 106 to provide a visual auditory and/or multi-stimulatory experience, system 100 essentially operates as a "multisensory microscope" to provide patient 108 with enhanced cognitive recognition and imprinting of their disease condition and the consequences of either treating or not treating the disease.

In one embodiment, system 100 may be considered to operate as a multi-scale and multisensory microscope, since system 100 provides virtual environment 106 to show patient 108 the present, future and even past effects of normal versus diseased physiology and pathophysiology readily, rapidly and interchangeably, as if spinning the turret of objectives on a microscope, allowing one to either "zoom in" or "zoom out" as to the actual biological. For example, system 100 may provide the experience of zooming in to see cellular, chemical, and physical consequences, and/or the experience of zooming out to see social, partner, spouse, family, group and society consequences of adherence or lack of adherence to therapy.

System 100, operating as a multi-scale microscope, may overlay the impact of adjunctive therapy in a multisensory (e.g., one or more of visual, tactile, taste, smell and auditory) way so patient 108 sees the benefit of the therapy and begins to develop a reinforcement cycle. This reinforcement cycle may then lead to the above described sensory shift where the patient experiences a positive sensation when practicing adherence to the therapy, e.g. warm feeling pleasant aroma, happiness and an overall sense of well-being. Examples of therapeutic overlays would include exercise e.g. jogging, cycling, swimming, yoga, pilates; meditation; weight loss; adequate sleep; stress avoidance; cessation of smoking; cessation of drinking; cessation of drug use and the like.

As shown in FIG. 6, system 100 may be considered "senso-ceutical." System 100 operates to provide cognitive recognition of a disease state (i.e., a condition having a clinical reality) by patient 108. That is, by immersing patient 108 within virtual environment 106, patient 108 is placed into an enhanced state of "getting it," since the provided immersive of "being in one's face" experience allows patient 108 to "close the loop." By closing the loop, patient 108 recognizes the disease, receives enhanced understanding and imprinting of the disease, and sensory elements may be further utilized as an effective therapy to lead to somatic processing with neuro hormonal, hormonal or neuroendocrine responses, and/or immunomodulation, and/or metabolic alteration which then invokes a therapeutic effect. For example, as described above, system 100 may be used to help patient 108 recognize the effects of atherosclerosis and gain understanding for the benefits of habitual adaptation and compliance to taking medication and/or a lifestyle change. Further, system 100, in the senso-ceutical case, provides an additional exogenous or extraneous sensory input to evoke positive somatic responses, which close the loop and provide a feedback-mediated enhanced amplified therapy.

In one example of operation, operator 405 configures patient 108 with virtual imager 420, audio output devices 422, actuators 424, O2 saturation sensor 440, and accelerometers 444. Operator 405 interacts with interface 404 to define one or both of a medical treatment being performed on patient 108 and a diagnosed disease of patient 108, and to instruct healthcare analytic engine 120, via controller 402, to select an optimal treatment model 406 for use with patient 108. Optionally, controller 402 may instruct operator 405, via interface 404, as to positioning and configuration of virtual imager 420, audio output devices 422, actuators 424, oxygen saturation sensor 440, and accelerometers 444 to optimally prepare patient 108 for treatment. Operator 405, via interface 404, may approve treatment model 406.

Treatment model 406 controls VITT driver 408 and PEGD driver 410 to control virtual environment 106 and provide both visual and physical experiences that simulate how the medical treatment is correcting the targeted disease. System 100 may also use adjunctive oral ingestion, such as, but not limited to, pills and drug therapy formulation. Virtual environment 106 provided by system 100 may be used as a stand-alone treatment modality or as an augmentation of current treatment. For example, experience 110 within virtual environment 106 provided by system 100 may be used to improve quality of life and extend life expectancy of Hepatocellular carcinoma patients.

In one embodiment, healthcare analytic engine 120 modifies treatment model 406 based upon analysis of therapy effectiveness as determined by healthcare analytic engine 120 for patient 108 and for other patients having a similar condition.

Table 1 shows exemplary parameters of treatment model 406.

TABLE 1

Embodiments:

| Therapy Target | VITT parameters | PEGD parameters |
|---|---|---|
| Atherosclerotic Coronary Disease | Images of artery with disease - as per the multi-scale microscope. Therapy e.g. drugs-statins, bypass surgery, angioplasty/stenting (all at multiple levels). | Pressure (of angina). Positive feeling massage, warmth, positive smell, - detailed in body above - all the positives. |
| Alzheimer's disease | Healthy brain, brain with dementia changes, restorative effects of drugs and other therapies. | Positive feeling massage, warmth, positive smell, - detailed in body above - all the positives |
| Hypertension | Images of health vessel, arterial changes with HTN, images of bleed/stroke | Pressure (of angina). Positive feeling massage, warmth, positive smell, - detailed in body above - all the positives |
| Diabetes | Images of obesity, atherosclerotic arteries, retinal damage, kidney damage, nerve damage, positive effects of weight loss, vascular improvements, kidney improvements, neurologic improvements | Pressure (of angina). Positive feeling massage, warmth, positive smell, - detailed in body above - all the positives |
| Obesity | Atherosclerositic changes (as above), fat accumulation, musculoskeletal changes, social effects, Positive effects of weight loss, exercise ability, social acceptance | Pressure (of angina). Positive feeling massage, warmth, positive smell, - detailed in body above - all the positives |

TABLE 1-continued

Embodiments:

| Therapy Target | VITT parameters | PEGD parameters |
| --- | --- | --- |
| COPD | Lung damage, infection, positive changes with smoking cessation, halting of disease progression | Positive feeling massage, warmth, positive smell, - detailed in body above - all the positives |
| Chronic Asthma | Bronchiolar changes, mucus buildup, risk medication of noncompliance, improvement of lung function with therapy. | Positive feeling massage, warmth, positive smell, - detailed in body above - all the positives |
| Chronic Pain | Inflamed nerves, inflammation at multiple sites, improvement with anti-inflammatories, ability to exercise | Positive feeling massage, warmth, positive smell, - detailed in body above - all the positives |

Figure 5:
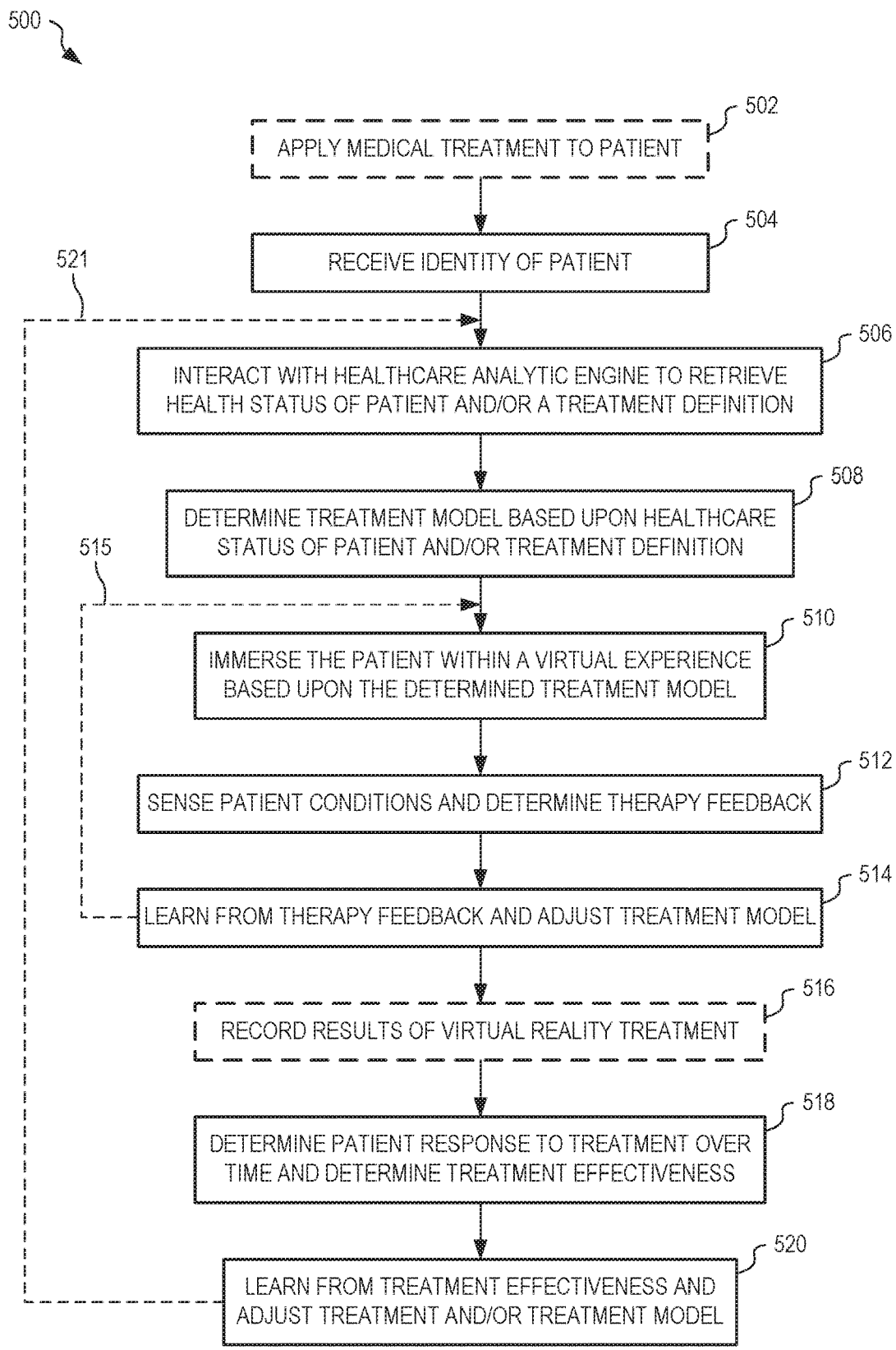
FIG. 5 is a flowchart illustrating one exemplary virtual reality method for improving clinical outcomes, in an embodiment.

FIG. 5 is a flowchart illustrating one exemplary virtual reality method 500 for improving clinical outcomes. Steps 504 through 510 are implemented within controller 402, FIG. 4, for example.

Step 502 is optional. If included, in step 502, method 500 applies a medical treatment to the patient. In one example of step 502, a doctor prescribes a medical treatment for a diagnosed disease of the patient. The medical treatment may be applied immediately prior to or during step 510, or may be applied some time previously.

In step 504, method 500 receives an identity of the patient. In one example of step 504, controller 402 receives an ID of patient 108 from operator 405 via interface 404. In step 506, method 500 interacts with the healthcare analytic engine 120 to retrieve a current health status of the patient and/or a treatment definition. In one example of step 506, controller 402 interacts with healthcare analytic engine 120 to receive one or both of complete health status 122 of patient 108 and treatment definition 123. In step 508, method 500 determines a treatment model based upon the healthcare status and/or the treatment definition. In one example of step 508, controller generates treatment model 406 based upon treatment definition 123. A treatment model is generated based on: (1) accurate diagnosis of the disease; (2) understanding the natural history of the disease and the typical response to therapy, as well as the specific patient's response to therapy—based on initial response and repeated interaction/visits with the patient (i.e. system 100 gets smarter by learning the patient's response to treatments in steps 514, 518, and 520); (3) health care giver—e.g. doctor informed decision making; (4) interactively with system 100 as it sees patient 108 repetitively and determines the effectiveness of response to initial therapy—i.e. the need of the enhanced virtual reality active component.

In step 510, method 500 immerses the patient within a virtual experience based upon the determined treatment model. In one example of step 510, controller 402 controls VITT driver 408 and PEGD driver 410 to generate control signals 104 to drive one or more of virtual imager 420, output devices 422, and actuators 424 to generate experience 110 within virtual environment 106.

In step 512, method 500 senses patient conditions and determines therapy feedback. In one example of step 512, sensor analyzer 412 reads sensors 440, 442, 444 and determines therapy feedback data for use by controller 402. In step 514, method 500 learns from therapy feedback and adjusts the treatment model. In one example of step 514, controller 402 receives feedback data from sensor analyzer 412 and uses learning algorithm 403 to update treatment model 406 based upon the feedback data. Steps 510 through 514 may repeat as indicated by arrow 515.

Step 516 is optional. If included, in step 516, method 500 records results of the virtual reality treatment. In one example of step 516, operator 405 provides input indicative of results of the virtual treatment on patient 108. In another example of step 516, healthcare analytic engine 120 automatically collects health information of patient 108.

In step 518, method 500 determines the patient's response to treatment over time and determines the treatment effectiveness. In one example of step 518, controller 402 determines effectiveness of one or both of medical treatment and the virtual reality treatment based upon sensed condition of patient 108 and health care data of patient 108 based upon one or more treatments over time. In step 520, method 500 learns from the treatment effectiveness and adjusts the medical treatment and/or treatment model. In one example of step 520, controller 402 uses learning algorithm 403 to recommend changes to the medical treatment, and/or adjusts treatment model 406 based upon input from sensor analyzer 412 and/or healthcare analytic engine 120. Steps 506 through 520 may repeat, as indicated by arrow 521.

Emotion, Behavior, and Psychology

Therapies are aimed at modulating the consciousness of the patient regarding their health and disease state, regarding their emotional, psychological, and behavioral engagement. In past times, such therapies were provided by the patient's doctor; however, in the modern world, the time available for a doctor to address the patient's condition is so reduced that the doctor has no time to provide therapy for modulating consciousness of the patient. However, mankind has gained knowledge into the workings of the brain, and has discovered that by modulating the consciousness of the patient's brain, the doctor may achieve neuro-endocrinologic and neuro-immunologic action when the patient is placed in a positive state for responding to therapy. The benefits of having a positive mental state are known. See, e.g., "Thinking, Fast and Slow" by Daniel Kahneman, ISBN-13: 978-0374533557.

In the modern world, a doctor does not have the time to interact at length with patient 108 to provide a full understanding of the medical treatment. Often, a patient leaves hospital with a prescription for one or more drugs without a full understanding of what each drug does and why they are taking it, or even when and how to best take each drug to limit drug interactions and interaction of the drug with food. Thus, the patient is not engaged emotionally, behaviorally, and psychologically, resulting is the drug treatment being less effective when taken, and often resulting in the patient's failure to comply in taking one or more of the drugs. The doctor may therefore use system 100 to increase the emotional, behavioral, and psychological engagement of patient 108 in the applied medical treatment. By creating this positive mental state within patient 108, the patient's brain generates neurotransmitter chemicals (e.g., a balance of dopamine and serotonin) that are very beneficial to the medical treatment. We know that there is a neurological-endocrine and neuro-immunologic connection when the right neurological signals are working within patient 108, such that the immune system and endocrine status are positively affected. In another example, where patient 108 is critically ill, but doesn't remain mentally engaged with the current medical treatment and indicates that they are giving up, it is an indication that they will probably soon die. Thus, even where patient 108 has a terminal illness, the use of system 100 provides positive thinking and allows the patient to keep the very important neuropsychological emotional axis with its appropriate biochemical mediators.

Within virtual environment 106, system 100 immerses patient 108 within a selected experience 110 based upon his or her own disease and healthcare, using a very impactful experience that affect patient 108 emotionally, behaviorally, and psychologically and results in a positive mental change that enhances performance of the medical treatment. System 100 first shows patient 108 the problems caused by the disease, and then shows patient 108 how the medical treatment affects the disease to improve the health of patient 108. Thus, experience 110 creates a positive mental attitude towards the disease within patient 108 together with a desire to improve the disease. System 100 provides a "concrete" experience for patient 108 by reinforcing the problems of not treating the disease and the benefits of treating the disease.

System 100 may be used to repeat this experience for patient 108 based upon the disease state. Psychology of learning indicates that this type of therapy is synergistic and augmentative oftentimes to conventional mechanical or pharmacological therapy. For example, if the patient is receiving a pill to control blood pressure, system 100 may provide experience 110 showing the impact of hypertension, patient 108 thereby better understands the reason for taking the pill, is more aware of their medical condition, learns how the drug in the pill works, and is thereby provided with a positive mental attitude that makes the drug work more effectively, thereby potentially reducing the need for more complex treatments requiring multiple medications, or invasive treatments such as a renal denervation (RDN) procedure.

System 100 generates experience 110 to provide a psychosomatic connection between the medical treatment and mental understanding of patient 108. Using somatic substitution, controller 402 controls PEGD driver 410 to drive actuators 424 to make experience 110 more real for patient 108. For example, if a person being tested on a performance receives a nice aroma in the background, that person often performs better than if they didn't receive the nice aroma. The nice aroma is for example a sweet pleasant smell that is not too strong. Controller 402 may therefore control PEGD driver 410 to operate actuator 424(3) to create a pleasant aroma for patient 108 within virtual environment 106. In another example, controller 402 controls PEGD driver 410 to operate actuator 424(4) to provide patient 108 with a pleasant taste at appropriate moments during experience 110, such that those moments are enhanced within the mind of patient 108.

In another example, patient 108 is obese. First, system 100 is used to generate experience 110 for patient 108 showing the effects of being obese on the human body. For example, by immersing patient 108 within experience 110 where controller 402 simultaneously controls (a) VITT driver 408 to generate imagery within virtual imager 420 showing how the arteries get clogged and (b) PEGD driver 410 to drive actuator 424(1) to tighten a strap positioned around the patient's chest. In another example, controller 402 simultaneously controls (a) VITT driver 408 to generate imagery showing how kidney function declines and (b) PEGD driver 410 to drive actuator 424(3) to provide a bad smell to patient 108. Then system 100 is used to generate experience 110 for patient 108 showing the effects when patient 108 corrects the disease. For example, by immersing patient 108 within experience 110 where controller 402 simultaneously controls (a) VITT driver 408 to generate imagery showing the patient exercising, and (b) PEGD driver 410 to drive actuator 424(3) to provide a fresh smelling breeze that is blown towards patient 108, and then (c) VITT driver 408 to generate imagery showing the arteries clearing and (d) PEGD driver 410 to drive actuator 424(1) to loosen the strap around the chest of patient 108. Experience 110 may extend where controller 402 simultaneously controls (a) VITT driver 408 to generate imagery showing images of patient 108 having lost weight, enjoying exercise without concern, jogging and playing in a park with other family members, (b) PEGD driver 410 to drive (i) audio output devices 422 (e.g., earphones) to provide sounds of bird singing, (ii) actuator 424(3) to provide the feeling and smell of fresh air, and so on. Where system 100 is used to provide multiple treatments, treatment model 406 may be selected to show patient 108 progressing further with exercise, such as riding a bicycle, swimming, and so on. Thus the progression of body improvement is reinforced by experience 110.

In another example of operation, patient 108 is being treated for heart failure but is not complying with recommended treatments and medications. In this example, system 100 determines, from healthcare analytic engine 120, that patient 108 is not complying with the medical treatment and generates treatment model 406 such that 402 controller controls VITT driver 408 and PEGD driver 410 to generate experience 110 to extrapolate the effects of non-compliance over time. For example, treatment model 406 may cause controller 402 to control VITT driver 408 to drive virtual imager 420 to first show images and effects of non-compliance by patient 108 after six months, where patient 108 is unable to walk far without getting out of breath, and then show images and effects of non-compliance by patient 108 after one year, where patient 108 becomes immobile, has swelling legs simulated by pressure applied to the patient's legs during the experience by actuators 424 driven by PEGD driver 410, and so on.

System 100 could then be used to generate experience 110 to show the effects when patient 108 conforms with the medical treatment (e.g., medication and/or exercise), where controller 402 controls VITT driver 408 to generate imagery showing images of patient 108 being able to walk more, participate in family activities, as so on.

Treatment model 406 and thus experience 110 may have generic components that may applies to patients having similar diseases and conditions, and have other components that are personalized for patient 108, such as images of patient 108 and other family members.

In one embodiment, at least part of experience 110 is implemented in game 130 (see FIG. 1), where the game may be experienced periodically at home by patient 108. Game 130 is configured by virtual environment generator 102 such that appropriate actions by patient 108 result in positive outcomes in game 130.

Similarly, system 100 may be implemented in a portable format (e.g., using a portable computer with a virtual reality headset, headphones, and so on) to allow experience 110 to be provided to patient 108 in almost any setting (e.g., at home, in the work place, in hospital, and so on).

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween. In particular, the following embodiments are specifically contemplated, as well as any combinations of such embodiments that are compatible with one another:

(A) A virtual reality system for improving clinical outcomes, includes: a virtual display device capable of providing virtual reality images to a patient; one or more actuators capable of providing physical experience to the patient; and a controller capable of: automatically selecting a treatment model based upon one or both of (a) a received identity of a medical treatment applied to the patient and (b) a received identity of a targeted disease of the patient; and coordinating the virtual display device and the one or more actuators to provide a synchronized immersive virtual reality environment for the patient to experience based upon the treatment model.

(B) In the virtual reality system denoted as (A), the controller further capable of selecting the treatment model to provide the synchronized immersive virtual reality environment to imprint and impart a somatic effect at a level lower than requiring thought from the patient.

(C) In either of the virtual reality systems denoted as (A) and (B), the one or more actuators imparting one or more of smell, sound, taste, temperature, massage, and other physical experiences to the patient.

(D) In any of the virtual reality systems denoted as (A)-(C), the treatment model being selected based upon historical results of previous uses of the virtual reality system.

(E) In any of the virtual reality systems denoted as (A)-(D), the synchronized immersive virtual reality environment being configured and controlled to induce a positive neuro-endocrine physiologic response from the patient.

(F) In any of the virtual reality systems denoted as (A)-(E), the positive neuro-endocrine physiologic response including a sense of well-being.

(G) In any of the virtual reality systems denoted as (A)-(F), the immersive virtual reality environment being configured to induce one or both of mild fear and anxiety.

(H) In any of the virtual reality systems denoted as (A)-(G), further including a sensor analyzer capable of (a) receiving input from one or more sensors coupled with the patient, and (b) providing feedback to the controller for modifying control of at least one of the virtual display device and the one or more actuators to provide the synchronized immersive virtual reality environment.

(I) In any of the virtual reality systems denoted as (A)-(H), the sensor analyzer capable of identifying, within the patient, one or more of: physiological, neurological, and neurohumoral effector responses including caudate nucleus activation, oxytocin release, and endorphin release.

(J) In any of the virtual reality systems denoted as (A)-(I), the controller further capable of learning from the effector responses.

(K) In any of the virtual reality systems denoted as (A)-(J), the controller further capable of identifying effectiveness of the treatment model.

(L) In any of the virtual reality systems denoted as (A)-(K), the controller further capable of modifying the treatment model based upon the identified effectiveness.

(M) In any of the virtual reality systems denoted as (A)-(L), the controller further capable of suggesting an alternative treatment model based upon the identified effectiveness.

(N) In any of the virtual reality systems denoted as (A)-(M), the treatment model defining the synchronized immersive virtual reality environment to simulate how the medical treatment is correcting the targeted disease.

(O) In any of the virtual reality systems denoted as (A)-(N), the controller selecting the treatment model based upon results indicating improved clinical outcome of the applied medical treatment when the treatment model was applied to other patients.

(P) In any of the virtual reality systems denoted as (A)-(O), the treatment model including multi-levels that provide an exogenous or extraneous sensory input to the patient to evoke positive somatic responses.

(Q) In any of the virtual reality systems denoted as (A)-(P), the treatment model defining the synchronized immersive virtual reality environment to implement multi-scale levels that include two or more of: (1) the whole body, (2) a body region, (3) an organ, (4) an organ component, (5) cellular, (6) intracellular, (7) molecular, and (8) atomic.

(R) In any of the virtual reality systems denoted as (A)-(Q), the synchronized immersive virtual reality environment invoking the multi-scale levels to allow the patient to experience elements of the physiology, pathophysiology, disease process, therapeutic process, and the consequences of wellness versus morbidity on multiple levels of involvement.

(S) In any of the virtual reality systems denoted as (A)-(R), the virtual reality system being implemented as a senso-ceutical to provide exogenous or extraneous sensory inputs to evoke positive somatic responses from the patient.

(T) In any of the virtual reality systems denoted as (A)-(S), the controller further capable of controlling the one or more actuators to administer a medication to the patient based upon the treatment model, the synchronized immersive virtual reality environment and the medication cooperating to synergistically enhance the experience and effect of the treatment model.

(U) In any of the virtual reality systems denoted as (A)-(T), the controller further capable of controlling the one or more actuators to administer a placebo to the patient based upon the treatment model, the synchronized immersive virtual reality environment and the placebo cooperating to synergistically enhance the experience and effect of the treatment model.

(V) In any of the virtual reality systems denoted as (A)-(U), the controller further capable of controlling the one or more actuators to stimulate the patient based upon the treatment model, the synchronized immersive virtual reality environment and the stimulation cooperating to synergistically enhance the experience and effect of the treatment model.

(W) In any of the virtual reality systems denoted as (A)-(V), the targeted disease being selected from the group including Anorexia Nervosa, CHF, Hypertension, Metabolic syndrome, and Chronic Pain.

(X) In any of the virtual reality systems denoted as (A)-(W), the targeted disease being a mechanistic target, the one or more actuators stimulating one or both of (a) afferent renal nerves to control Hypertension, and (b) vagus nerves to clinically improve disease condition in one or both of metabolic syndrome and chronic pain.

(AA) A virtual reality method for improving clinical outcome for a patient, including: receiving one or both of (a) an identity of a medical treatment applied to the patient and (b) an identity of a targeted disease of the patient; automatically selecting a treatment model based upon the identified medical treatments and targeted diseases; generating, using both a treatment therapy virtual display device to provide virtual reality images to the patient and one or more actuators that provide physical experience to the patient, an immersive virtual reality environment based upon the treatment model; and immersing the patient in the immersive virtual reality environment.

(AB) The virtual reality method denoted as (AA), further including interacting with a healthcare analytic engine to automatically select the treatment model based upon results of treatment plans used on patients having one or both of the identified medical treatments and targeted diseases.

(AC) Either of the virtual reality methods denoted as (AA) and (AB), further including interacting with the healthcare analytic engine to store results of the effect of the immersive virtual reality environment on the clinical outcome of the medical treatment on the patient.

(AD) Any of the virtual reality methods denoted as (AA)-(AC), further including automatically modifying the treatment model based upon based upon results, received from the healthcare analytic engine, of treatment plans used on patients having one or both of the identified medical treatments and targeted diseases.

(AE) In any of the virtual reality methods denoted as (AA)-(AD), the treatment model defining the immersive virtual reality environment to simulate how the medical treatment is correcting the targeted disease.

(AF) Any of the virtual reality methods denoted as (AA)-(AE), further including applying the medical treatment to the patient while the patient is immersed within the virtual reality environment.

(AG) Any of the virtual reality methods denoted as (AA)-(AF), further including applying the medical treatment to the patient prior to the patient being immersed within the virtual reality environment.

(AH) In any of the virtual reality methods denoted as (AA)-(AG), the virtual reality environment providing an experience based upon the treatment model to improve clinical outcome of the medical treatment.

(AI) In any of the virtual reality methods denoted as (AA)-(AH), the step of generating including generating the immersive virtual reality environment to implement multiscale levels that include two or more of: (1) the whole body, (2) a body region, (3) an organ, (4) an organ component, (5) cellular, (6) intracellular, (7) molecular, and (8) atomic.

(AJ) In any of the virtual reality methods denoted as (AA)-(AI), the step of generating including generating the immersive virtual reality environment to impart multisensory experiences at more than one of the multi-scale levels to the patient.

(AK) Any of the virtual reality methods denoted as (AA)-(AJ), further including: receiving input from one or more sensors coupled with the patient; and modifying the immersive virtual reality environment based upon the input.

(AL) Any of the virtual reality methods denoted as (AA)-(AK), further including identifying, based upon the input, one or more of: physiological, neurological, and neurohumoral effector responses including caudate nucleus activation, oxytocin release, and endorphin release.

(AM) Any of the virtual reality methods denoted as (AA)-(AL), further including learning from the effector responses.

(AN) Any of the virtual reality methods denoted as (AA)-(AM), further including identifying effectiveness of the treatment model.

(AO) Any of the virtual reality methods denoted as (AA)-(AN), further including modifying the treatment model based upon the identified effectiveness.

(AP) Any of the virtual reality methods denoted as (AA)-(AO), further including suggesting an alternative treatment model based upon the identified effectiveness.

(AQ) Any of the virtual reality methods denoted as (AA)-(AP), further including administering a medication to the patient based upon the treatment model, the synchronized immersive virtual reality environment and the medication cooperating to synergistically enhance the experience and effect of the treatment model.

(AR) Any of the virtual reality methods denoted as (AA)-(AQ), further including administering a placebo to the patient based upon the treatment model, the synchronized immersive virtual reality environment and the placebo cooperating to synergistically enhance the experience and effect of the treatment model.

(AS) Any of the virtual reality methods denoted as (AA)-(AR), further including stimulating the patient based upon the treatment model, the synchronized immersive virtual reality environment and the stimulation cooperating to synergistically enhance the experience and effect of the treatment model.

(AT) In any of the virtual reality methods denoted as (AA)-(AS), the targeted disease being selected from the group including Anorexia Nervosa, CHF, Hypertension, Metabolic syndrome, and Chronic Pain.

(AU) In any of the virtual reality methods denoted as (AA)-(AT), the immersive virtual reality environment including one or both of (a) afferent renal nerve stimulation to control Hypertension, and (b) vagus nerve stimulation to clinically improve disease condition in one or both of metabolic syndrome and chronic pain.

What is claimed is:

1. A virtual reality method for improving clinical outcome for a patient, comprising:
    receiving one or both of (a) an identity of a medical treatment applied to the patient and (b) an identity of a targeted disease of the patient;
    automatically selecting a treatment model based upon the identified medical treatments and targeted diseases;
    generating, using both a treatment therapy virtual display device to provide virtual reality images to the patient and one or more actuators that provide physical experience to the patient, an immersive virtual reality environment based upon the treatment model; and
    immersing the patient in the immersive virtual reality environment.

2. The virtual reality method of claim 1, further comprising interacting with a healthcare analytic engine to automatically select the treatment model based upon results of treatment plans used on patients having one or both of the identified medical treatments and targeted diseases.

3. The virtual reality method of claim 2, further comprising interacting with the healthcare analytic engine to store results of the effect of the immersive virtual reality environment on the clinical outcome of the medical treatment on the patient.

4. The virtual reality method of claim 2, further comprising automatically modifying the treatment model based upon based upon results, received from the healthcare analytic engine, of treatment plans used on patients having one or both of the identified medical treatments and targeted diseases.

5. The virtual reality method of claim 1, the treatment model defining the immersive virtual reality environment to simulate how the medical treatment is correcting the targeted disease.

6. The virtual reality method of claim 1, further comprising applying the medical treatment to the patient while the patient is immersed within the virtual reality environment.

7. The virtual reality method of claim 1, further comprising applying the medical treatment to the patient prior to the patient being immersed within the virtual reality environment.

8. The virtual reality method of claim 1, the virtual reality environment providing an experience based upon the treatment model to improve clinical outcome of the medical treatment.

9. The virtual reality method of claim 1, the step of generating comprising generating the immersive virtual reality environment to implement multi-scale levels that include two or more of: (1) the whole body, (2) a body region, (3) an organ, (4) an organ component, (5) cellular, (6) intracellular, (7) molecular, and (8) atomic.

10. The virtual reality method of claim 9, the step of generating comprising generating the immersive virtual reality environment to impart multisensory experiences at more than one of the multi-scale levels to the patient.

11. The virtual reality method of claim 1, further comprising:
receiving input from one or more sensors coupled with the patient; and
modifying the immersive virtual reality environment based upon the input.

12. The virtual reality method of claim 11, further comprising identifying, based upon the input, one or more of: physiological, neurological, and neurohumoral effector responses including caudate nucleus activation, oxytocin release, and endorphin release.

13. The virtual reality method of claim 12, further comprising identifying effectiveness of the treatment model.

14. The virtual reality method of claim 13, further comprising modifying the treatment model based upon the identified effectiveness.

15. The virtual reality method of claim 13, further comprising suggesting an alternative treatment model based upon the identified effectiveness.

16. The virtual reality method of claim 1, further comprising administering a medication to the patient based upon the treatment model, the synchronized immersive virtual reality environment and the medication cooperating to synergistically enhance the experience and effect of the treatment model.

17. The virtual reality method of claim 1, further comprising administering a placebo to the patient based upon the treatment model, the synchronized immersive virtual reality environment and the placebo cooperating to synergistically enhance the experience and effect of the treatment model.

18. The virtual reality method of claim 1, further comprising stimulating the patient based upon the treatment model, the synchronized immersive virtual reality environment and the stimulation cooperating to synergistically enhance the experience and effect of the treatment model.

19. The virtual reality method of claim 1, the targeted disease being selected from the group including Anorexia Nervosa, CHF, Hypertension, Metabolic syndrome, and Chronic Pain.

20. The virtual reality method of claim 1, the immersive virtual reality environment including one or both of (a) afferent renal nerve stimulation to control Hypertension, and (b) vagus nerve stimulation to clinically improve disease condition in one or both of metabolic syndrome and chronic pain.

* * * * *